(12) United States Patent
Ming

(10) Patent No.: US 7,726,314 B1
(45) Date of Patent: Jun. 1, 2010

(54) NEBULIZER, FILTER OR INHALANT MASK ENCOURAGING USE THEREOF

(76) Inventor: Christopher Koo Khim Ming, 85B Sungai Karangan, 09410 Padang Serai, Kedah (MY)

( * ) Notice: Subject to any disclaimer, the term of this patent is extended or adjusted under 35 U.S.C. 154(b) by 463 days.

(21) Appl. No.: 11/635,107

(22) Filed: Dec. 6, 2006

(51) Int. Cl.
*A62B 18/08* (2006.01)

(52) U.S. Cl. .................... 128/206.12; 128/205.25; 128/205.27; 128/206.11; 128/206.16; 128/206.18; 128/206.19; 128/206.21; 128/206.24; 128/206.26; 128/206.27; 128/206.28; 128/207.11; 128/207.12; 128/207.13; 128/207.18; 128/202.27; 128/204.18; 128/204.21; 128/204.23; 128/203.12; 128/203.15; 128/203.29

(58) Field of Classification Search ............ 128/205.25, 128/205.27, 206.11, 206.12, 206.16, 206.18, 128/206.19, 206.21, 206.24, 206.26, 206.27, 128/206.28, 207.11, 207.12, 207.13, 207.18, 128/202.27, 204.18, 204.21, 204.23, 203.12, 128/203.15, 203.29
See application file for complete search history.

(56) References Cited

U.S. PATENT DOCUMENTS 6,192,876 B1 * 2/2001 Denyer et al. .......... 128/205.25
7,082,947 B2 * 8/2006 Smaldone .............. 128/206.23

* cited by examiner

*Primary Examiner*—Patricia M Bianco
*Assistant Examiner*—Nihir Patel

(57) ABSTRACT

The present invention is a generally conical nebulizer, aerosol, filter or inhalant face mask for sealing against the atmosphere a wearer's mouth and nose, the improvement comprising a representation of a face on the outside surface with an exhaust valve located where the mouth would be located. The exhaust valve is adapted to visibly lift outward and up from the outside mask surface to imitate a flapping tongue.

1 Claim, 4 Drawing Sheets

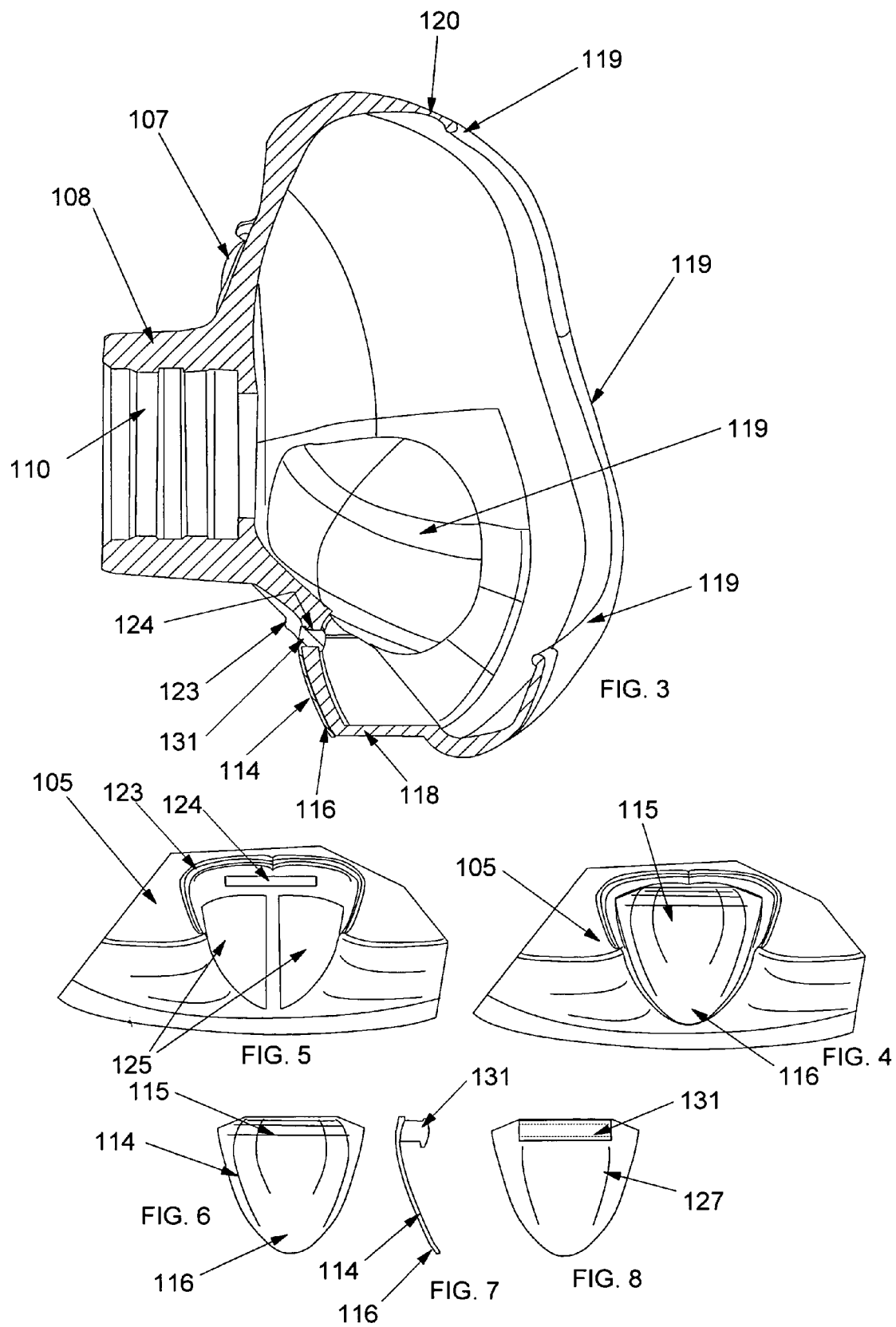

NEBULIZER, FILTER OR INHALANT MASK ENCOURAGING USE THEREOF

FIELD OF THE INVENTION

The present invention relates to nebulizer, filter or inhalant masks, especially with reference to those adapted for use by children.

BACKGROUND OF THE INVENTION

Nebulizer, filter or inhalant masks are well known to provide human-to-nebulizing equipment connection for delivery of atomized liquids and aerosols. The lungs can be easily penetrated by medicinal aerosols and provides a convenient and generally safe vehicle for obtaining rapid absorption of medication by the body. Medication or drugs are generally delivered to the lung membrane in the form of a fine mist or aerosol which is breathed into the lungs through the nose or mouth of the patient. Quite typically, a nebulizer is used to convert a liquid into a fine aerosol, and the aerosol is introduced into the lungs by means of a face mask which delivers the aerosol through the mouth and nose of the patient. However, conventional face masks have been consistently designed with medical necessity and cost minimization in mind over patient acceptance of the face mask. It is known that inhalant systems incorporating a face mask are often repeatedly used by a patient in order to treat what is usually a long term, repeating or chronic illness. Although providing an aerosol to the lungs of some medications is clearly preferable to injection or oral medications, it is a rather dreary prospect to the patient.

It is well known in the art of holiday celebration to provide decorative masks for revelers. These ornamental masks have no function other than to provide entertainment in the context of the celebration and often bear relatively accurate representations of famous persons or fantastical faces. Regardless of their basis in reality or fantasy, most of such ornamental face masks bear a two or three dimensional representation of a face with at least a nose and eyes, most often with a mouth of some sort. Most persons from a very early age are exposed to such ornamental masks and associate them with rather happy memories. Even a fleeting view of such ornamental masks brings to mind happier times. Such ornamental masks bear the faces of clowns, animals, cartoon characters, and other brightly colored entities.

There is a need for a face mask that combines the benefits of ornamental face masks with the functions of face masks for receiving aerosol or nebulized liquids so that children and young persons are thereby encouraged to engage in what is sometimes a frightening or dreary experience for them.

SUMMARY OF THE INVENTION

The present invention is a generally conical nebulizer, aerosol, filter or inhalant face mask for sealing against the atmosphere a wearer's mouth and nose, the improvement comprising a representation of a face on the outside surface with an exhaust valve located where the mouth would be located. The exhaust valve is adapted to visibly lift outward and up from the outside mask surface to imitate a flapping tongue. This is a truly hilarious effect.

In an alternate embodiment of this invention, one or more exhaust valves are located amount the facial features so that when activated the valves imitate flapping ears, nose, eyes or eyelids.

It is well known in the medical arts that face masks for inhaling liquids in the form of aerosols, vapors, gases or nebulized liquids or dry powderized medications in the form of fine, dry particles for medical purposes should be generally conical in shape. Such a mask from the wearer's side comprises a conical concavity which is ringed at a peripheral edge with a soft, compressible material so that a user's mouth and nose area can be sealed off against the outside air for receiving said liquids or powders for medical purposes. Said liquids or powders are delivered with oxygen containing gas to the wearer through an opening generally at the bottom of the wearer's side concavity. That opening extends through the mask shell to a cylindrical extension upward from the outside surface of the mask to connect with a rigid or flexible conduit bearing the liquids or powders to the wearer. In order to economize and reduce mask weight, the mask is a shell so that the outside surface facing away from the user is generally conical in shape.

The effect of viewing such a mask from the outside is that the cylindrical hose connector could be imagined to be very large nose. The downward-sloping conical surfaces away from the nose connection can bear facial features of an ornamental mask used in holiday celebrations. The facial features of such ornamental masks are arranged on the outside surface of the invention mask referencing the location of the hose connector as the nose on such a face.

Creating facial features on such a mask is relatively easy. Features such as the lips of a large, smiling mouth can be painted or mold-formed on the part of the downward sloping outside surface that broadens in an inferior direction to accommodate a wearer's mouth. Features such as or large, striking and happy looking eyes, eyelids, brightly colored hair and/or prominent colorful ears can be painted or mold-formed on the part of the downward sloping outside surface that narrows in a superior direction from the hose connector to capture a wearer's nose without covering or impressing upon a wearer's eyes.

It is critical in a sealed breathing circuit using such a mask to provide for the wearer a valve or vent to the atmosphere for exhausted breath. Examples of such exhaust valves are well known in the art. Exhaust valves in one form generally use a thin septum connected in one part to a conduit in the breathing circuit. The thin septum is supported over and seals the openings of a fenestrated frame so that the thin septum rises off the openings when a slight positive pressure is imposed on the breathing circuit. Operation of the exhaust valves vents is not optional. A wearer should not be burdened by the simple act of exhalation during a medical procedure for inhalation of vapors, gases or nebulized liquids. The positive pressure required to open the exhaust valve should be quite low with respect to the external atmospheric pressure. The exhaust valve should react almost instantaneously upon initiation of exhalation of a user. Placement of the exhalation valve close to a wearer's nares or mouth provides the fastest response to opening of the valve at the initiation of exhalation.

Even adult wearers of nebulizer masks don them with some apprehension. For children, the unknown operation of the breathing circuit with its complicated, strange-looking, noisy and/or odd smelling equipment terminating in a mask to be attached to a child's face is a potentially frightening event. The present invention locates a fenestrated frame and its sealing thin septum at a location on a face mask shell where a viewer might associate the location of a mouth if eyes are formed or painted in a position superior to the hose connector. In other words, if eyes are seen above the hose connector on the outside surface, a viewer would tend to look below the hose connector on the outside surface of the mask for mouth features. In a preferred embodiment, the thin septum of the exhaust valve is red with one end free to lift off the fenestrated frame during exhalation of a wearer in a manner that would imitate the flapping of a tongue. In most cultures, wagging or flapping a tongue is a comic event. In the present invention, it is a comic relief and encouragement to a child wearer of the mask to engage in such flapping of their face mask "tongue".

BRIEF DESCRIPTION OF THE DRAWINGS

FIG. 3 is section 117 of the mask of FIG. 2.

FIG. 4 is a close-up and cutaway view of a lower part of the mask of FIG. 2 with an exhaust valve in place and in a sealed and closed position.

FIG. 5 is a close-up and cutaway view of a lower part of the mask of FIG. 4 with the exhaust valve removed.

FIGS. 6, 7 and 8 are respectively frontal, side and rear views of the exhaust valve of FIG. 4.

DETAILED DESCRIPTION OF THE INVENTION

The invention is now discussed with reference to the figures.

Figure 1:
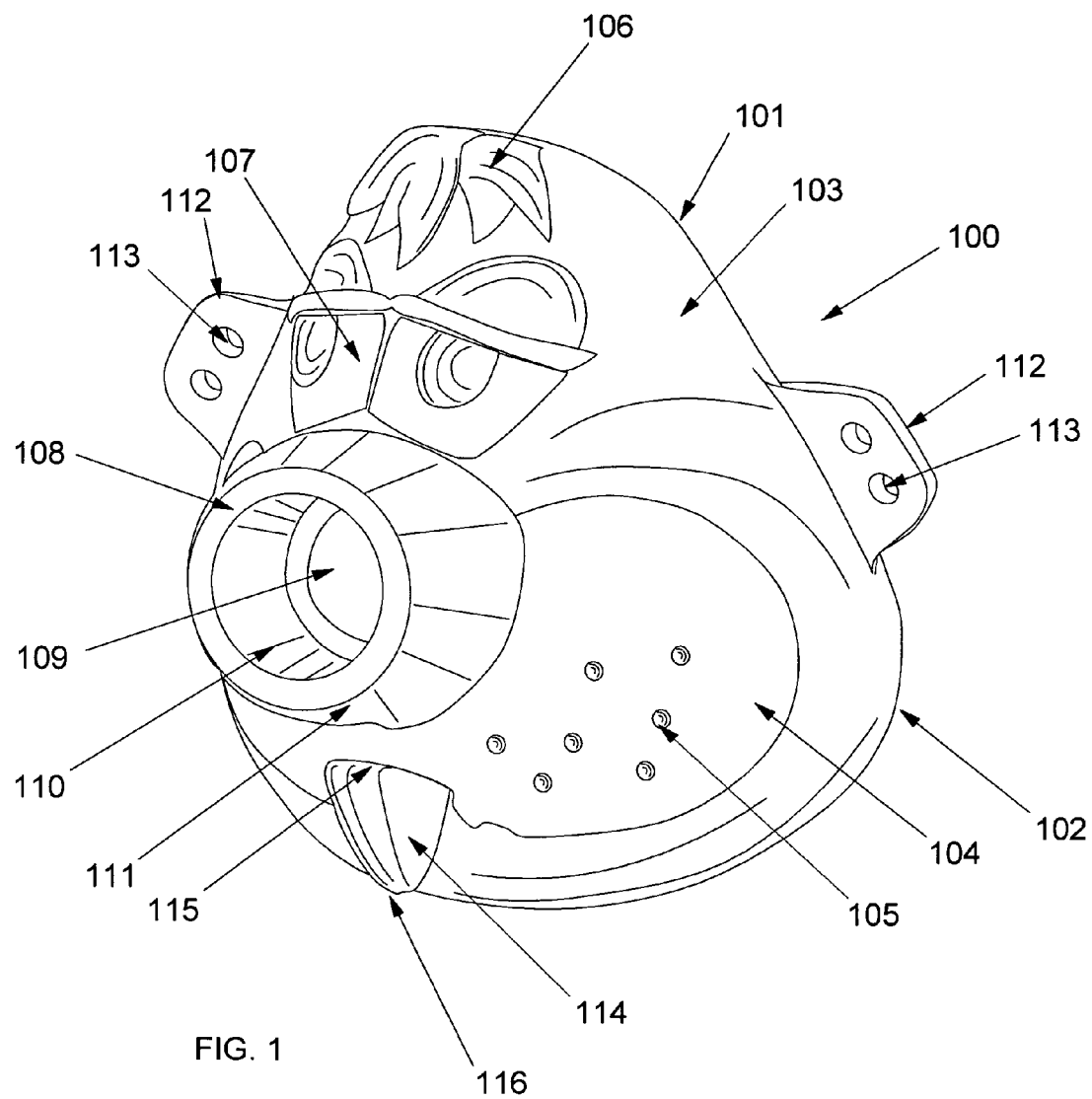
FIG. 1 is a perspective view of the outside surface an invention mask bearing an ornamental representation of a face.

FIG. 1 shows invention mask 100 comprising a lower portion 101 and upper portion 102, respectively having lower outside surface 104 and upper outside surface 103. An ornamental cheek and lip part 105 is shown extending generally from side to side with ornamental freckles, a middle part of which defines an upper lip above tongue valve 114. Valve 114 is an exhaust valve for a wearer's exhalations adapted to be actuated when positive pressure is exerted on the inside space of the mask 100 when sealed to a wearer's face surfaces. Valve 114 comprises a more rigid attachment end 115 and flapping tongue end 116.

Mask 100 further comprises a hose connector 108 which defines a cylindrical passage 109 by inside surface 110. Surface 110 is adapted to receive a hose or other gas conduit end so that gas and aerosols can be delivered to a mask wearer. Hose connector 108 preferably has an outward and downward sloping outside surface 111 having an slightly acute angle with reference to inside surface 110. Outside surface 111 for hose connector 108 thus more closely resembles a nose to a frontal viewer of the outside surface of mask 100. Thus far in the description, an ornamental face on mask 100 has been described bearing a cheeks and an upper lip above a tongue adapted to flap up and down during a wearer's exhalation and a large nose represented by the outside surfaces of the hose connector 108.

On lateral sides of mask 100 are formed extensions 112 with holes 113 for straps that can secure mask 100 to a wearer's head. Extensions 112 may be formed in the shape of large or small colorful ears with reference to the cheek and lip with reference to what a viewer would construe to be an ornamental face with a nose at hose connector 108.

On the upper surface 103 of mask 100 are representations of eyes 107 and hair 106. It should be understood that the form, shape, size, colors, emotion and other aspects of such eyes and hair may vary widely while achieving the objects of the invention, i.e., encouraging or entertaining a user and/or viewer of mask 100 while observing the flapping valve 114 on an ornamental face.

Figure 2:
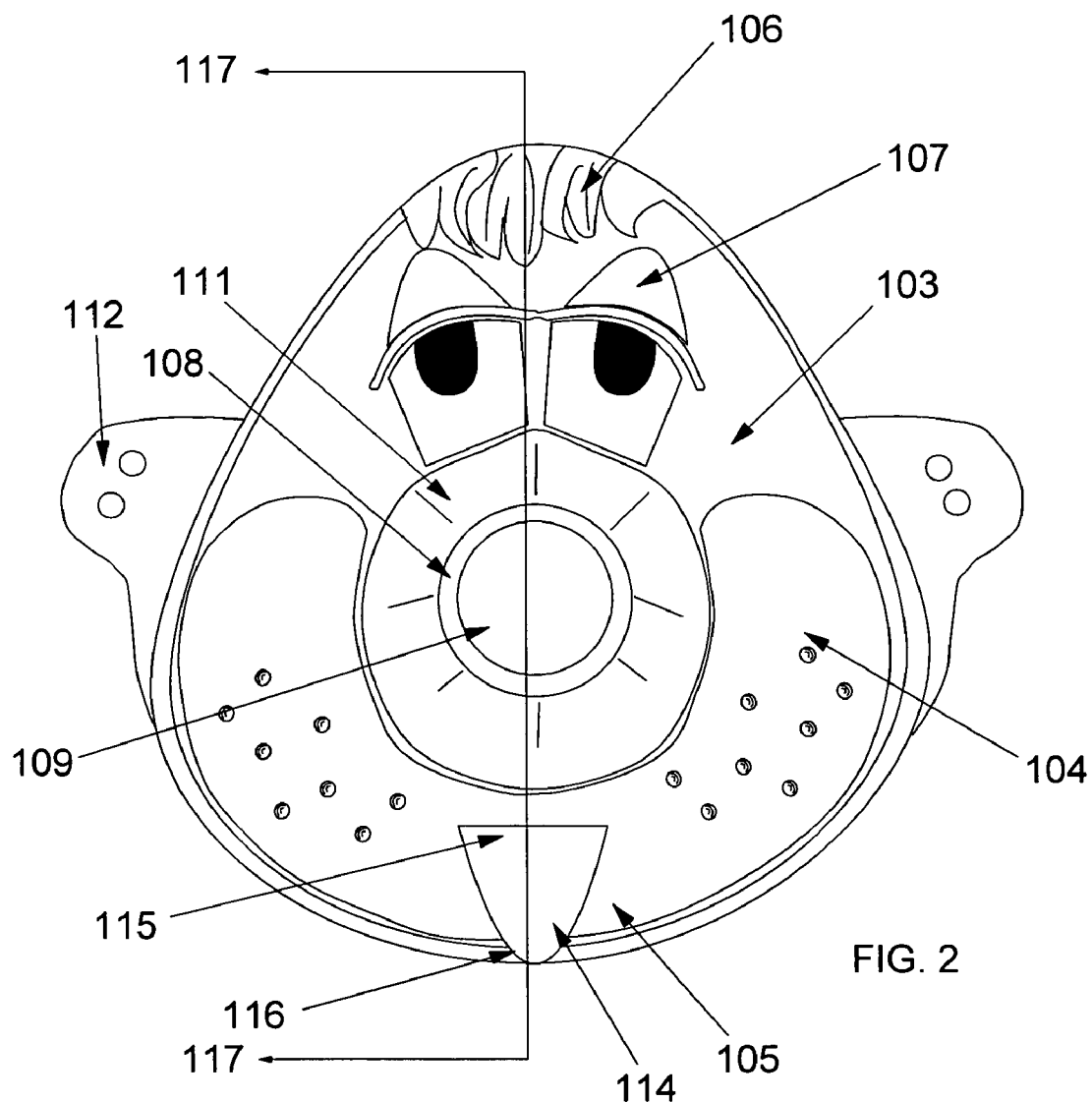
FIG. 2 is a frontal view of the mask of FIG. 1.

FIG. 2 is a frontal view of the mask of FIG. 1 and shows how a viewer would typically see a mask 100 worn by a user. It is part of the objects of the invention that the user would know that a viewer would see a flapping tongue valve 114 while the user uses mask 100. Such activity entertains the user to be able to wag their "tongue" at a viewer.

FIG. 3 is section 117 of the mask of FIG. 2 showing a ribbed surface 110 adapted to engage a gas conduit connected thereto. Mask 100 further comprises in one embodiment a soft sidewall 120 with rim 119 that compress and seal to the facial skin of a mask wearer. Frame part 126 is shown in cross section supporting the under side of valve 114 and connects to a top edge of shell wall part 118. Attachment end 115 is shown secured in slot 124, leaving a flexible thin septum end 116 distal to end 115. FIGS. 6, 7 and 8 are respectively frontal, side and rear views of the exhaust valve 114 of FIG. 4 showing that valve 114 is formed of an elastomeric material appropriate for a valve of this type in a curved shape so that when it is connected in slot 124 (FIGS. 3 and 5) at flange 126, end 116 effectively seals openings 125 (FIG. 5). FIG. 5 shows that lips 123 may be formed in surface 105 to define an upper edge of the "tongue" shape of valve 114. Valve 114 is preferably formed of a bright red elastomeric material. FIGS. 6 and 7 further show that valve 114 comprises a concave inside surface 127 adapted to seal openings 125 (FIG. 5).

Figure 9:
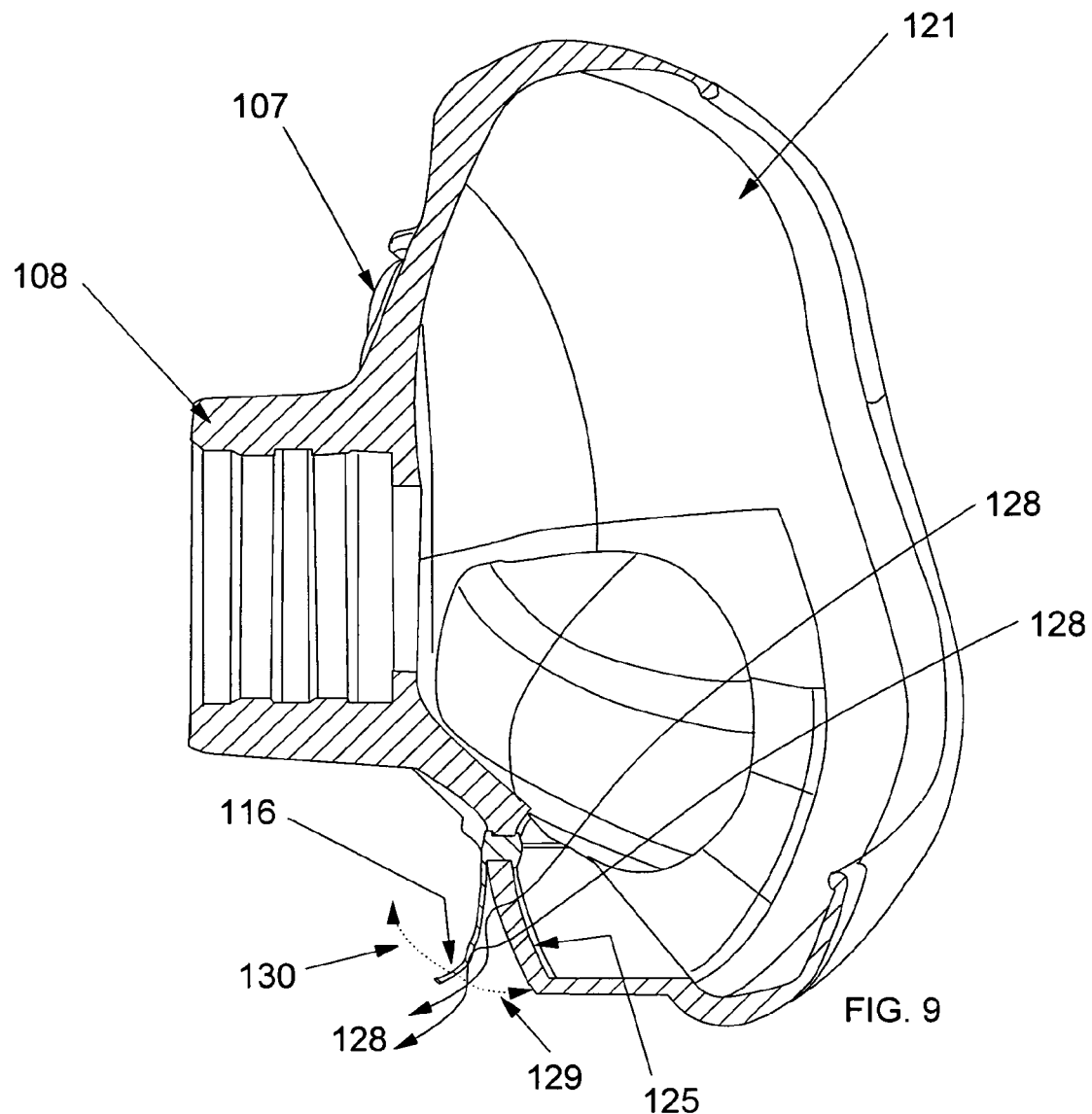
FIG. 9 is view of FIG. 3 with the end of the exhaust valve flapping open during exhalation by a wearer.
Figure 10:
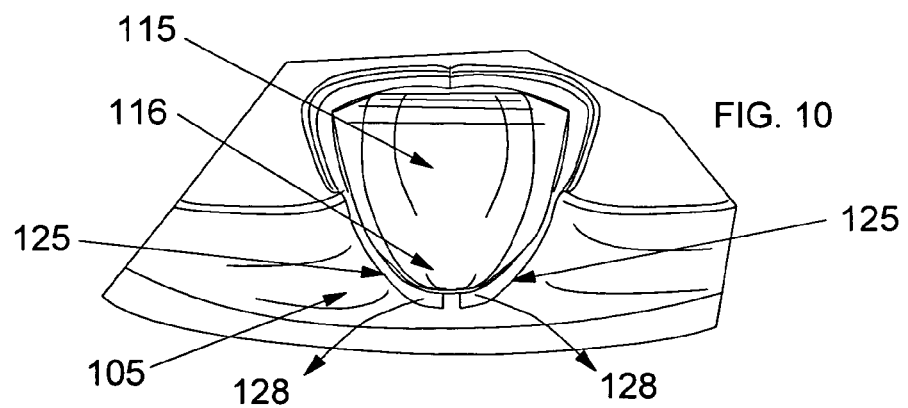
FIG. 10 is a close-up and cutaway view of a lower part of the mask of FIG. 2 with an exhaust valve in place and the septum end flapping open during exhalation by a wearer.

FIGS. 9 and 10 show how end 116 of the exhaust valve 114 flaps to an open position along path 130 during exhalation by a wearer. Exhaust air travels along paths 128 through openings 125, forcing upward and outward end 116, giving the viewer the impression of a wagging or flapping tongue. At the end of the exhalation by a wearer, valve 114 returns to the position shown in FIGS. 1, 2, 3 and 4 along path 129.

The above design options will sometimes present the skilled designer with considerable and wide ranges from which to choose appropriate apparatus and method modifications for the above examples. However, the objects of the present invention will still be obtained by that skilled designer applying such design options in an appropriate manner.

I claim:

1. A face mask for sealing against the atmosphere a wearer's mouth and nose and supplying pressurized inhalant gas and providing means for exhalation from a patient engaged to the face mask, the improvement comprising a generally conical shell comprising a hose connector cylinder, a representation of a face on an outside surface of said shell, whereby an outward extension of the hose connector cylinder from the shell appears to form a nose of said face representation, and an exhaust valve in a location where an external viewer of the face mask would associate with a location of a mouth of the face representation;

the exhaust valve comprises a flexible component, so that when a patient is engaged to the face mask and exhales into the shell, the flexible component elevates from a surface defined by a surrounding portion of an outside surface of the shell in imitation a flapping tongue of the face representation;

the face representation comprises representations of one or more eyes on the outside surface of the shell opposite the location of the hose connector cylinder;

the shell further comprises formed extensions at lower portions of the shell near to or extending from said peripheral edge, said formed extensions being adapted to engage with straps to secure the face mask to a patient's head and having a shape and location so that an external viewer would associate said formed extensions with ears of the face representation;

the shell further comprises an exhaust opening defined in the location of the exhaust valve, the exhaust opening being interrupted by support extensions from the shell for support of a flexible portion of the exhaust valve;

the flexible component further comprises an attachment end which is secured to the shell at a position proximal to the hose connector cylinder and a flexible portion which extends to sealingly cover the exhaust opening when a patient using the face mask is not exhaling; and the face representation comprises representations of a lip or lips on the outside surface of the shell surrounding the location of the exhaust valve.

* * * * *